United States Patent
Dal Farra et al.

(10) Patent No.: US 7,413,755 B2
(45) Date of Patent: Aug. 19, 2008

(54) USE OF A COTTON HONEYDEW EXTRACT AS ACTIVE INGREDIENT IN OR FOR PREPARING A COSMETIC AND/OR PHARMACEUTICAL COMPOSITION

(75) Inventors: Claude Dal Farra, Opio (FR); Nouha Domloge, Valbonne (FR); Dominique Peyronel, Marseille (FR)

(73) Assignee: Societe d'Extraction des Principes Actifs S.A., Biot (FR)

( * ) Notice: Subject to any disclaimer, the term of this patent is extended or adjusted under 35 U.S.C. 154(b) by 413 days.

(21) Appl. No.: 10/537,359

(22) PCT Filed: Dec. 2, 2003

(86) PCT No.: PCT/FR03/03557

§ 371 (c)(1),
(2), (4) Date: Jun. 3, 2005

(87) PCT Pub. No.: WO2004/052331

PCT Pub. Date: Jun. 24, 2004

(65) Prior Publication Data

US 2006/0018868 A1    Jan. 26, 2006

(30) Foreign Application Priority Data

Dec. 3, 2002  (FR) .................................. 02 15189

(51) Int. Cl.
*A61K 36/00*        (2006.01)

(52) U.S. Cl. ..................................................... 424/725
(58) Field of Classification Search .................. None
    See application file for complete search history.

(56) References Cited

U.S. PATENT DOCUMENTS 6,306,906 B1 *  10/2001  Wohlman et al. ............ 514/552
2004/0132978 A1 *  7/2004  Fahnestock et al. ......... 530/353

FOREIGN PATENT DOCUMENTS

EP        0 622 487         2/1994
JP        10025240 A  *    1/1998

OTHER PUBLICATIONS

Database WPI Section Ch, Week 199916, Derwent Publication ltd., London, GB; AN 1999-186170 XP002256877 & JP 11 035428 A (Shiseido Co Ltd) Feb. 9, 1999 abstract.
Database WPI, Section Ch, Week 199513, Derwent Publicatiions Ltd., London, AN 1995-093730, XP002256878 & JP 07-017824, Jan. 20, 1995.

* cited by examiner

*Primary Examiner*—Christopher R Tate
*Assistant Examiner*—Deborah A. Davis
(74) *Attorney, Agent, or Firm*—Young & Thompson

(57) ABSTRACT

The invention concerns the use, as active principle, in or for preparing a composition, of an efficient amount of at least one extract of cotton honeydew, the extract or the composition being designed for care of keratinous substrates. The invention also concerns a cosmetic and/or pharmaceutical composition containing said extract, and a method for cosmetic treatment of the skin using said cotton honeydew extract or the composition containing same.

21 Claims, No Drawings

USE OF A COTTON HONEYDEW EXTRACT AS ACTIVE INGREDIENT IN OR FOR PREPARING A COSMETIC AND/OR PHARMACEUTICAL COMPOSITION

The present invention relates to the cosmetic and pharmaceutical fields, more particularly the field of dermatology.

The present invention has as an aim the use, as an active ingredient, in or for the preparation of a composition, of an efficient amount of at least a cotton honeydew extract, in which the extract or composition is intended for the care of keratin substrates.

The skin is the major keratin substrate of an organism. It is a vital organ covering the whole surface of the body which ensures multiple functions such as sensitive functions, protective functions from external aggressions, as well as immunological, metabolic or thermoregulatory functions. These roles are made possible due to a complex structure which associates various tissues.

The skin consists of three superimposed distinct layers: epidermis, dermis and hypodermis. The epidermis is a coating epithelium which constitutes the external structure of the skin and provides its function of protection. This function is provided by the cohesion of the epithelial cells and by the production of a filamentous and resistant protein, keratin. The epidermis is organized in a strate-like manner corresponding to an increasing state of differentiation of keratinocytes (cell representing more than 80% of the cell population of the epidermis) from the deepest area (basal stratum) to the most superficial area (stratum corneum). During the migration towards the surface of the skin, keratinocytes undergo biochemical and structural modifications, the most significant being keratinization, a process through which cells synthesize keratin. The basal layer (stratum corneum) is thus very resistant against external aggressions.

Keratin is the essential compound of all keratin substrates such as capillary fibers, hair, nails and other superficial body growths. Keratin is thus a very significant molecule at the level of the pilous follicle. It is produced by keratinocytes located at the bottom of the pillar bulb which multiply and differentiate. Some spread out at the periphery of the pilous follicle to form the external and internal epithelial sheaths, and others stretch out to form the pillar stem. Over the course of their migration, keratinocytes become filled with keratin fibers, which makes hair very resistant. Therefore, the amount of keratin in the cell plays a significant role, most notably in all the phenomena of protection.

Health and cosmetics specialists have been searching for numerous years for the means in order to maintain keratin substrates, in particular skin and hair, as well as for the means to increase skin and hair resistance against the external aggressions and stress they are subject to every day. A certain number of substances introduced in cosmetic or pharmaceutical products were developed, but improvements still remain to be made in order to use cosmetic or pharmaceutical products which are capable of regulating these problems in a satisfactory manner.

The technical problem to solve has thus been, for the inventors, to find a new substance, that is cosmetically or pharmaceutically acceptable, and which is capable of bringing veritable care to keratin substrates but also to protect the skin and hair in an efficient manner so that they don't are subject to degradations caused by aggressions and stress from external origins.

The inventors have succeeded in selecting particular substances that display remarkable properties when they are applied to a keratin substrate. In an unexpected manner, the inventors have discovered that an efficient amount of at least a cotton honeydew extract has remarkable properties at the level of keratin substrates, and in particular that it protects the skin and the hair.

Cotton is the group of fibers (or hair) covering the cottonseed. The cotton plant, or *Gossypium*, is a dicotyldon belonging to the Malvaces family. There are from 40 to 50 species which can be perennial or annual, and ligneous or herbaceous. Only four of them are cultured for their fiber: *Gossypium hirsutum, Gossypium barbadense, Gossypium herbaceum* and *Gossypium arboreum*. These four species gave birth to numerous hybrid varieties, sorted according to the length of their fiber, the pubescent seed and the form of the bract. It is the *Gossypium hirsutum* cotton plant line which alone provides 80 to 90% of the world cotton production. The cotton fruit is a resistant and oval capsule which contains numerous seeds covered in white and tight hairs (or fibers) of different lengths.

Cotton holds a predominant place among the natural textile fibers such as hemp, linen and burlap. Thanks to the progress of industrial techniques, as well to agricultural research, cotton has been the first fiber of the world since the 19th century. Their linters, the down which remains on the seeds after ginning, are also highly sought-after by the chemical industries, additionally its seed, containing from 16 to 18% of edible oil, plays an increasing role in human and animal food.

Honeydew designates a product, present in the plants, which contains sugars synthesized by certain insects as well as sugars of physiological origin, that is to say, synthesized by the plant itself. This product settles on plants after being partly excreted by insects, such as whiteflies and aphids (Gameel, 1996) as they feed on plants. Therefore, the honeydew is found on the plants and it makes a sticky substance. This phenomenon is particularly problematic in the case of cotton where the contamination through honeydew is one of the most harmful factors for cotton fibers and poses serious problems for the textile industry.

To the knowledge of the applicant, it has never been described, in the former art, the use of cotton honeydew extracts in cosmetic and/or pharmaceutical and/or dermatological compositions. Up to today, only cottonseed oil, as well as cotton fibers have been used in cosmetics, such as in U.S. Pat. No. 5,466,441 patent or in the EP 1092425 patent.

Thus, the present invention has for an object the use, as an active ingredient, in or for the preparation of a composition, of an efficient amount of at least a cotton honeydew extract; the extract or composition being intended for the care of keratin substrates.

The word <<extract>> designates any product or preparation which is obtained from dry vegetable substance (or animal). It is obtained, for instance, by dissolution of the active ingredients using solvents (such as water, alcohol or even ether), then by concentration of the active ingredients, for instance, by evaporation of the solvents. By the term "honeydew cotton extract", we refer to all isolated substances obtained from the plant raw material which constitutes cotton, and more particularly cotton fibers. The extract will contain the maximum of extractable compounds. By the term "honeydew cotton extract" we refer, in particular, to any extract containing sugars collected from cotton fibers. According to the invention, cotton honeydew, which is obtained by a classical method of extraction well known by the person skilled in the art, will allow the possibility to obtain a composition containing different types of molecules found in cotton fibers, and in particular constitutive of this honeydew.

These molecules could be, more especially, the various types of sugars constitutive of this honeydew. It is well understood that the extract can be prepared from cotton of at least one of the numerous varieties and species of cotton plants.

The active ingredient may be defined as a molecule or a group of molecules likely to bring modifications or modulations to the function of a biological system.

In the invention, by the term "keratin substrate" we refer to all substrates which are primarily composed of keratin. They are substrates such as skin, hair, eyelashes, eyebrows, and even nails or superficial body growths in general.

The care of keratin substrates refers to all the actions intended to conserve or restore the correct functioning of this substrate or any means which helps preserve or improve its appearance and/or its aspect. Thus, care refers to hydration, appeasement, protection against all types of aggressions, including, in particular, sun care, and the fight against and prevention of the manifestations of aging, especially the manifestations of cutaneous aging.

Modifications of cutaneous aging include all of the modifications regarding the external appearance of skin that result from aging, such as wrinkles, fine lines, limp skin, slackened skin, slimmer looking skin, loss of elasticity and/or skin tone, dull skin, and skin which lacks radiance. It also includes internal skin modifications that do not translate directly into changes in the external appearance of the skin. An example of these internal modifications is the internal skin degradation resulting from consecutive exposure to UV radiation.

Hair and skin are sensitized and weakened to different degrees by the action of atmospheric agents and by light, as well as by more or less aggressive treatments, such as perms, dye, hair bleaching, chemical detergent products, soaps, and make-up for skin. In the long run, the mechanical properties of hair and skin, such as resistance or elasticity, are altered. This alteration is due, for the most part, to a more or less significant damage of keratin.

For hair and/or skin cleansing and/or washing, the use of detergent lotions (such as shampoos and other soaps) essentially composed of classical tensioactives, in particular anionic, non-anionic and/or amphoteric types, but more particularly, the anionic type, is common. These compositions are applied to wet keratin substrates and the foam made by the massage allows, after rinsing with water, the elimination of different dirty marks that were initially present.

Though these compositions wash effectively, but the cosmetic properties that are attached to them are, however, low considering the relatively aggressive character of such a cleansing treatment. Indeed, this treatment can, in the long run, cause more or less marked and various damages to capillary fibers and/or skin. These types of damage are linked, in particular, to the progressive elimination of proteins contained in or on the surface of capillary fibers and skin. Thus, to improve the cosmetic properties of the above detergent compositions, a solution is to introduce complementary cosmetic agents, principally intended to repair or limit the harmful and adverse reactions induced by the different treatments or aggressions which capillary fibers and skin are subjected to. These cosmetic agents could be, for example, cotton honeydew extract according to the invention.

The invention has, as a second object, the use, as an active ingredient, in or for the preparation of a composition, of an efficient amount of at least a honeydew cotton extract; the extract or composition being intended to protect keratin substrates, and more particularly to protect the skin and/or the hair from all types of external aggressions. According to the invention, the cotton honeydew extract or the composition containing it is advantageously used for hair protection.

The use of cotton honeydew extract will allow the keratin substrates to be protected and will therefore enable them to better resist stress that the environment produces. The term "external aggression" refers to the aggressions that the environment can produce. These aggressions can be of chemical, biological or thermal origin. These aggressions include pollution, UV, friction, water with high limestone concentration, temperature variations or even irritating products such as tensioactives, preservatives or perfumes. The types of aggression experienced by the skin and hair are due, for example, to the instability of the electrochemical gradient through the cell membrane, which can lead to significant variations in osmotic pressure and may result in osmotic shocks and therefore cell lysis.

But the inventors have demonstrated, in a surprising manner, that the extract according to the invention allows the cells to be protected against osmotic shocks. Moreover, it has been demonstrated that the extract according to the invention allows a protection against damage caused to the cell's DNA, particularly that the extract according to the invention allows the cell's DNA to be protected when it is subject to stress such as when the cell is nutrient deprived. These protective properties can be used to develop compositions intended to protect skin and/or hair against external aggressions induced, in particular, by the action of sunlight or by other physical, chemical or biological agents. These protective properties can also be used to make compositions enabling the fight against cutaneous aging.

Moreover, the invention has for an object the use, as an active ingredient, in or for the preparation of a composition, of an efficient amount of at least a cotton honeydew extract; the extract or composition being intended to increase the synthesis of proteins of the keratin substrates. Indeed, the applicant has demonstrated that the extract according to the invention enables the increase of the protein of keratinocyte synthesis, particularly that the extract according to the invention enables an increase in keratin synthesis.

Thus, according to another variant of the invention, the aforementioned active ingredient increases protein expression of the skin and/or improves protein stability. This protein can be representative of the proliferation and/or differentiation of skin cells, more particularly of the cells of the dermis and the epidermis. Notably, keratin is indicative of the proliferation and/or differentiation of keratinocytes, more precisely it is representative of keratinocyte differentiation. Therefore, the extract according to the invention plays a role in cell differentiation.

According to the invention, the extract has a positive action on tissue regeneration.

Thus, it has been demonstrated that cotton honeydew extract has the ability to reinforce keratin of the hair and skin, and more generally on all keratin substrates. Additionally, it possesses the ability to protect against the effects of light.

The invention also has for an object the use, as an active ingredient, in or for the preparation of a composition, of an efficient amount of at least a cotton honeydew extract; the extract or composition being intended to reinforce the cutaneous barrier and/or to reinforce hair. Moreover, this cotton honeydew extract provides excellent cosmetic properties for hair and skin.

The invention also relates to the use, as an active ingredient, in or for the preparation of a composition, of an efficient amount of at least a cotton honeydew extract; the extract or composition being intended to nourish keratin substrates. Indeed, the applicant has demonstrated that the extract according to the invention allows an increase in the survival of keratinocytes when the cells are nutrient deprived. The extract according to the invention allows the cells to better resist stress, in particular stress caused by nutrient deficiencies. The extract according to the invention improves cell survival. The invention also relates to the use, as an active ingredient, of an efficient amount of at least a cotton honeydew extract; the extract or composition being intended to hydrate keratin substrates.

Thus, cotton honeydew extract according to the invention, or the composition containing it, is particularly well adapted to the care of keratinocyte materials, especially for hair care.

Cotton honeydew extract is essentially constituted of sugars. It is composed, in particular, of sugars such as glucose, fructose, saccharose, trehalose, trehalulose or even melezitose. Cotton honeydew can also contain inositol. According to an advantageous mode of realization, cotton honeydew possesses sugars present in defined proportions. Thus, preferentially, fructose can represent from 30 to 40% of the total amount of sugars present in the honeydew, glucose can represent from 20 to 35%, saccharose from 3 to 20%, melezitose from 0 to 10%, trehalulose from 0 to 6%, trehalose from 0 to 10% and inositol from 0 to 12% of the total amount of sugars present in the honeydew.

Any method of extraction of cotton honeydew can be used to prepare the extract according to the invention.

Thus, as an example, the extraction process of cotton honeydew can be performed in several steps. Firstly, the honeydew present on the fibers is extracted from cotton with a solvent. This solvent can be from different origins, it can be composed of water and/or of organic solvent (methanol, ethanol, isopropanol, acetone . . . ) and/or any other substance which has the property to dissolve the sugars.

Preferentially, according to the invention, the extraction is performed with a mix of water and ethanol; the proportion of alcohol varies from 0 to 100%. The extraction can be performed at different temperatures, at room temperature or at a higher temperature, up to 100° C.

Secondly, according to a variant of the extraction process, an enzymatic complex, promoting the extraction, can be added. As another step, after cotton honeydew extract, the extract can be concentrated by evaporation at atmospheric pressure or in a vacuum. The extract is then put in an appropriate solvent, and is sterilized. The extract can then be used in this form.

In a variant of the invention, the cotton honeydew extract can be subject to a hydrolysis treatment, either chemically or by contact with a microorganism or with an enzymatic complex. The extract can also be subject to different treatments of bleaching by contact with absorbent substances, active coal or even bleaching earth. The extract can, in the same manner, be subject to treatments of purification and fractioning by the technique of crystallization or by a process such as chromatography.

The extract according the invention can be of different natures; we can cite, in particular, aqueous, alcoholic extracts or those using an organic solvent. An aqueous solvent refers to any solvent constituted totally, or in part, of water. Such solvents can be water, hydro alcoholic solvents in all proportions or even solvents constituted of water and a compound such as butylene glycol, in all proportions. Among alcoholic solvents ethanol is an example. This extract can be obtained by dissolution in water, alcohol or ether, then by concentration of this solution performing evaporation or distillation.

To give an order of magnitude, we can use the extract according to the invention in a quantity representing from 0.0001% to 20% of total weight of the composition and preferentially in a quantity representing from 0.01% to 10% of total weight of the composition.

According to an advantageous mode of realization of the invention, the above mentioned extract is first solubilized in one or several cosmetically or pharmaceutically acceptable solvents such as water, ethanol, propanol or isopropanol, propylene glycol, butylene glycol, dipropylene glycol, ethoxylated or propoxylated diglycols, cyclic polyols, vaseline, a vegetable oil or any mix of these solvents.

According to another advantageous mode of realization of the invention, the above mentioned extract is first solubilized in a cosmetic or pharmaceutical vector such as liposomes or adsorbed on powdery organic polymers, mineral supports such as talc and bentonites, and more generally solubilized in, or fixed on, any cosmetically or pharmaceutically acceptable vector.

According to another aspect, the invention has for object a composition characterized in that it contains, as an active ingredient, in a cosmetically or pharmaceutically acceptable medium, at least a cotton honeydew extract such as previously defined.

According to the invention, the composition can be a cosmetic and/or a dermatological and/or pharmaceutical composition. According to the invention, the composition is preferably cosmetic and/or dermatological and/or pharmaceutical in nature, since it is aimed at improving the cutaneous appearance and general cutaneous performance of the individual who uses it.

According to the present invention, the composition is preferably a cosmetic and/or dermatological composition adapted for topical cutaneous application through an acceptable cosmetic or dermatological medium.

According to a preferred mode of realization, the composition is especially well adapted to the use of hair care.

It is evident that the invention relates to mammals in general, and more specifically, to humans.

The effective amount of active ingredient corresponds to the necessary amount in order to obtain the desired result. According to an advantageous mode of realization, the above mentioned cotton honeydew extract is present in the compositions of the invention at a concentration between approximately 0.0001% to 20%, and preferably at a concentration between approximately 0.01% and 10% by weight relative to the total weight of the composition.

Whatever forms the invention takes, the composition, according to the invention, can be ingested, injected, or, applied to skin (to all cutaneous zones of the body), hair, nails or mucous membranes. According to the mode of administration, the composition related to the invention can be presented under all galenic forms normally used.

The compositions related to the invention are preferably presented under a galenic form adapted for cutaneous topical administration and adapted for administration on hair. They cover all the cosmetic and dermatological forms. These compositions must contain an acceptable cosmetic or dermatological medium. That is to say, a medium that is compatible with skin and hair. These compositions can take the form of an aqueous, hydro-alcoholic or oil solution; or the form of oil-in-water, water-in-oil emulsions or in multiple emulsions. They can also be used as creams, as a suspension or as a powder, adapted for application to skin, mucous membranes, lips and/or hair. These compositions can also be more or less fluid or solid and can take the form of creams, lotions, milks, serums, ointments, shampoo, gel, paste and mousse. It can also take a solid form like a stick, or it can be used on the skin or in aerosols. It can also be used as a skin care product and/or as make-up for skin. Concerning injection, the composition related to the invention can be an aqueous or oil based lotion or a serum. For application to the eyes, the composition can be used as drops whereas for ingestion it can be used as capsules, granules, syrup or pills.

Moreover, these compositions can include all of the additives that are usually considered for use in this application including all the possible additives necessary for their formulation such as solvents, thickeners, diluents, anti-oxidants, colorants, solar filters, auto-tanning products, pigments, fillers, preservatives, perfumes, odor absorbers, pharmaceutical and cosmetic active ingredients, essential oils, vitamins, essential fatty acids, tensioactivators, filmogen polymers etc. . . .

In all the cases, the person skilled in the art will attempt to carefully consider the selection of adjuvants, as well as their proportions, so as not to compromise the advantageous properties of the composition relating to the invention. These adjuvants can, for example, correspond to 0.01% to 20% of the total weight of the composition. When the composition according to the invention is an emulsion, the fatty phase can represent 5% to 80% by weight, but preferably it would represent 5% to 50% of the weight with respect to the total weight of the composition. Emulsifiers or co-emulsifiers used in the composition are selected among those that are classically used in the domain under consideration. For example, they can be used in a proportion of 0.3% to 3% by weight relative to the total weight of the composition.

Of course, the person skilled in the art should select the complementary compounds for the composition, active or non-active, as well as the amounts of the complementary compounds in such a way that the advantageous properties of the composition will not be perceptibly altered by the envisaged addition.

The compositions, according to the present invention, can be applied most notably as a cosmetic or pharmaceutical composition for use on the skin, mucous membranes and/or semi-mucous membranes. The compositions can be applied, particularly, as hair protection and/or hair care products.

We can also consider an application in the field of facial and body make-up compositions, such as lipsticks, foundation, tinted creams, dark circle sticks, or sunscreen and artificial tanning compositions.

The compositions of the invention can be used in a great number of treatments, notably cosmetic and dermatological treatments. They can take the form of cosmetic compositions used for skin, lips and/or hair treatment, protection, care and make-up removal and/or cleaning, as well as for make-up applications for skin, lips, eye lashes and/or the body. The composition relating to the invention can also consist of solid preparations such as soap and other cleaning bar soaps. The composition can also be made in aerosol form in which it can be mixed with pressurized propulsion agents. The composition can also be used orally, for example, as toothpaste. The composition of the invention can be applied as a cosmetic, dermatological or pharmaceutical composition to be used orally. These can take the form of drinkable solutions, syrups, tablets, sugar coated pills, capsules, or even as food and nutritional supplements.

According to the invention, we can add to the composition of the invention, other active agents intended for the prevention and/or treatment of the manifestations of cutaneous aging, and/or hair protection from external aggressions. According to the invention, the composition can be intended to form a protective filter for the keratin substrates. According to the invention, the use of cotton honeydew extract can be considered in a curative and/or preventive manner.

According to another aspect, the present invention also relates to a cosmetic process of treatment for the care of keratin substrates and more particularly for skin care and/or hair care consisting in applying, to the surface of the skin and/or the hair, an effective amount of cotton honeydew extract such as previously defined, in order to obtain the desired action. The present invention relates to, in the same manner, a cosmetic process of treatment in order to protect the keratin substrates against all types of external aggressions.

Particular modes of realization of this cosmetic process of treatment also result from the preceding description.

According to another aspect of the invention, the present invention relates to a cosmetic process of treatment in order to reinforce the cutaneous barrier of the skin and/or improve the protection of hair. According to another aspect of the invention, the present invention relates to a cosmetic process of treatment in order to increase keratin synthesis and/or in order to nourish the skin. The process of cosmetic treatment related to the invention can be implemented, particularly, when applying the cosmetic compositions here above according to methods habitually used for compositions, such as the application of creams, gels, serums, lotions, milks, shampoo, and sun creams, on skin, hair and as a toothpaste applied to the gums.

According to a particular mode of realization of this cosmetic process, cotton honeydew extract can be used for the preparation of a detergent composition or for the preparation of washing powders. Indeed, according to the invention cotton honeydew extract has a remarkable efficiency for the maintenance and protection of natural or synthetic fibers.

Thus, according to another aspect of the invention, the invention has for an object the use, in or for the preparation of a composition, of an efficient amount of at least a cotton honeydew extract; the extract or the composition being intended for the maintenance and/or protection of natural or synthetic fibers.

Other advantages and characteristics of the invention will become apparent by reading the following examples, by way of an illustrative and unrestrictive demonstration of data.

EXAMPLE 1

Preparation of Cotton Honeydew Extract

First, honeydew is extracted from cotton fibers with a solvent, the aforementioned solvent is constituted of a water-ethanol mix; the proportion of alcohol varies 0% to 100%.

Then, as a second step, sugars are extracted from cotton by hydrolysis with an enzymatic cocktail, then the pH of the reaction should be comprised between 4 and 8, and the temperature to between 35 and 65° C.

The principal sugars extracted are glucose, fructose, saccharose, trehalose, melezitose, trehalulose and inositol.

The yield of the extraction is 0.3%. The final concentration in sugars is between 50 and 100 g/l.

The sugars are then presented in an aqueous or hydro alcoholic solution, and they are sterilized by heating at 65° C. for 12 hours.

EXAMPLE 2

Demonstration of the Effect of Cotton Honeydew Extract on Keratin Expression

The aim of the study is to determine the influence of the extract according to the invention, on keratin synthesis, by keratinocytes, using the immunofluorescence technique, which is a semi-quantitative technique that enables the determination of the amount of each of the proteins present in the cell cytoplasm.

Keratin expression has been studied in human skin sections cultured for 24 hours. Two applications of 0.5% cotton honeydew extract (diluted in PBS at 0.5%) were applied on skin sections. The effect of the extract was assessed in comparison with skin sections not treated with the honeydew extract according to the invention. After the application, the skin samples were cultured for 24 hours, and were then prepared for inclusion in paraffin. Immunoblotting was then performed using an anti-keratin antibody. The detection of the amount of keratin was performed by immunofluorescence.

The results obtained show that the application of the extract according to the invention, on skin sections, causes an increase in keratin synthesis. This stimulation was observed in a significant manner in comparison with non-treated sections. Indeed, when the skin sections are incubated in the presence of the composition containing the active ingredients, we observe an increase in fluorescence intensity. This translates as a stimulation of keratin synthesis by keratinocytes.

EXAMPLE 3

Demonstration of the Nutritive Effect of Cotton Honeydew on Keratinocytes

The aim of the study is to demonstrate the nutritive effect of the extract, according to the invention, on keratinocytes.

This effect was measured using a cellular viability test on nutrient deprived cells.

The study was performed on HaCaT human keratinocytes, in an exponential growth phase in Lab-Tek™. Keratinocytes were cultured in 96-well plates. Cells were pre-treated for 2 hours with the active ingredient. Then the culture medium (with or without active ingredient) is replaced by PBS for 3h30, in the presence or absence of the active ingredient. Cells maintained in PBS (without the active ingredient) for 3h30 served as a control condition.

MTT tests were carried out to evaluate cellular viability.

In a general manner, the MTT agent is used to evaluate the cytotoxicity of a product compared with a cellular medium using cellular viability measurements.

Keratinocytes are cultured in a solution containing 0.1 mg/ml of MTT (3-[4,5-dimethylthiazol-2-yl]-2,5-diphenyltetrazolium bromide). This compound is adsorbed by the living cells, then metabolized by mitochondrial enzymes (succinate deshydrogenase) into a blue-purple compound, formazan, in the form of purple crystals that are insoluble in aqueous medium. Formazan crystals dissolved in DMSO give an absorbance (Abs) that is proportional to the number of the living cells present in the sample. Absorbance measurements were performed for each sample studied (Abs is read at 540 nm). Absorbance is directly proportional to enzymatic activity as well as to the number of living cells.

The results showed that the cells cultured in PBS, which have been totally nutrient deprived, are subjected to a very intense stress and alter rapidly. In the same manner, these measurements showed that depending on the concentrations of the extract that are used, the cells treated with the aforementioned extract have a viability which increases from 15% to 30% with respect to non-treated cells. These results clearly showed that cotton honeydew extract, according to the invention, has a significant nutritive power at the cellular level.

EXAMPLE 4

Demonstration of the Protective Effect of Cotton Honeydew Against Osmotic Shock

The aim of the study is to show the protective effect of cotton honeydew against osmotic shock on keratinocytes. This effect was measured using a cellular viability test on cells subjected to osmotic shock.

The study was performed on HaCaT human keratinocytes in an exponential growth phase in Lab-teks™. Then, cells were treated for 1 hour with 0.5% cotton honeydew extract. Then, the culture medium was removed and the cells were exposed to a hyper tonic solution (DMEM+NaCl 500 mM) for 1 hour in the presence or absence of the active ingredient. A MTT test was carried out to evaluate cellular viability.

The test result showed that cell viability was diminished by half when cells were subjected to osmotic stress. Moreover, the results showed that cotton honeydew increased keratinocyte viability by 37% compared to control cells, which were not treated with the active ingredient, but, which were subjected to osmotic shock.

EXAMPLE 5

Demonstration of the Effect of Cotton Honeydew Extract on DNA Protection

The aim of the study is to demonstrate the ability of the extract, according to the invention to protect keratinocyte DNA. The effect was measured using the "Comet test" on cells subjected to a significant stress.

The same test used in example 3 was performed: the cells were subjected to a stress caused by a nutrient loss ("food starvation"). After this stress, a study of DNA protection was carried out, using the Comet test, in order to evaluate DNA degradation of the cells treated with cotton honeydew extract in comparison with cells not treated with the extract.

The Comet test, or "Single Cell Gel Electrophoresis" is a short and sensitive micro electronic technique that enables simple and double-strand DNA breaks to be visualized. After treatment, cells are trapped in an agarose gel and lysed in a highly salinity buffer containing detergents. Then, the DNA is denatured using an alcaline bath followed by a short electrophoresis, and it is visualized using propidium iodine. DNA of an altered cell migrates towards the anode in proportion to the number of strand breaks and forms a comet. DNA that is significantly degraded is located in the "tail" of the comet. A cell, which is intact, remains round; DNA remains compacted at the level of the comet's "head". The evaluation of DNA lesions is performed using a software that allows the determination of the percentage of DNA degradation.

The results demonstrated that the cells subjected to "food starvation" underwent a stress and their DNA is degraded.

Moreover, the results demonstrated that DNA protection of the cells treated with cotton honeydew was increased by 60% with respect to control cells (non-treated by the active ingredient but subjected to stress). Therefore, cotton honeydew has a significant role in the protection of DNA.

EXAMPLE 6

Preparation of Compositions

These compositions were obtained by a simple mixture of the various components. The quantities indicated are expressed as percent by weight.

1. Emulsion oil-in-water

| INCI names | Massic % |
| --- | --- |
| OILY PHASE | |
| Cetearyl Alcohol (and) Cetearyl Glucoside | 5.00 |
| Simmondsia Chimensis Seed Oil | 5.00 |
| Paraffinum Liquidum (Mineral oil) | 5.00 |
| Isopropyl Palmitate | 7.00 |
| AQUEOUS PHASE | |
| Glycerin | 5.00 |
| Allantoin | 0.10 |
| Extract according to example 1 | 1.00 |
| Polyacrylamide (and) C13–14 Isoparaffin (and) Laureth-7 | 0.30 |
| Conservative | 0.50 |
| Perfume (Fragrance) | 0.50 |
| Aqua (Water) | Qsp |

2. Lotion

| INCI names | Massic % |
| --- | --- |
| Propylene Glycol | 1.00 |
| Allantoin | 0.30 |
| Glycerin | 1.00 |
| PEG-7 Glyceryl Cocoate | 1.00 |
| Extract according to example 1 | 0.01 |
| Conservative | 0.20 |
| Perfume (Fragrance) | 0.50 |
| Aqua (Water) | qsp |

3. Gel

| INCI names | Massic % |
| --- | --- |
| Carbomer | 25.00 |
| triethanolamine | 0.50 |
| Extract according to example 1 | 0.50 |
| Conservative | 0.20 |
| Tetrasodium EDTA | 0.10 |
| Perfume (Fragrance) | 0.50 |
| Water-soluble Stain | Qsp |
| Aqua (Water) | Qsp |

4. Shampoo

| INCI names | Massic % |
| --- | --- |
| Sodium Laureth Sulfate | 30.00 |
| Cocamidopropyl Betaïne | 6.00 |
| Polysorbate 20 | 2.00 |
| PEG-120 Methyl Glucose Dioleate | 0.75 |
| Tetrasodium EDTA | 0.10 |
| Sodium Chloride | 1.00 |
| Extract according to example 1 | 1.00 |
| Conservative | 0.30 |
| Perfume (Fragrance) | 0.50 |
| Colorant | Qsp |
| Aqua (Water) | Qsp |
| Citric Acid | qsp pH = 5.5–6.0 |

The invention claimed is:

1. A method for treating a keratin substrate, comprising applying an effective amount of at least a cotton honey dew extract or composition comprising a cotton honeydew extract to the keratin substrate.

2. A method to protect skin and/or hair against external aggressions, comprising applying an effective amount of at least a cotton honey dew extract or composition comprising a cotton honeydew extract to the skin and/or hair.

3. A method to increase keratin substrate synthesis, comprising applying an effective amount of at least a cotton honey dew extract or composition comprising a cotton honeydew extract to the keratin substrate.

4. A method to reinforce the cutaneous barrier of the skin and/or to reinforce the protection of hair, comprising applying an effective amount of at least a cotton honey dew extract or composition comprising a cotton honeydew extract to the skin and/or hair.

5. A method to nourish keratin substrates, comprising applying an effective amount of at least a cotton honey dew extract or composition comprising a cotton honeydew extract to the keratin substrates.

6. The method according to claim 1 wherein the cotton honeydew extract contains sugars selected from the group consisting of glucose, fructose, saccharose, trehalose, melezitose, trehalu lose and inositol.

7. The method according to claim 1 wherein the sugars present in cotton honeydew extract are 30 to 40% fructose, 20 to 30% glucose, 3 to 20% saccharose, 0 to 10% melezitose, 0 to 6% trehalulose, 0 to 10% trehalulose and 0 to 12% inositol as a percentage of the total quantity of sugars present in the honeydew.

8. The method according to claim 1 wherein the cotton honeydew extract is used in proportions between 0.0001% and 20%, by weight, relative to the total weight of the composition.

9. A cosmetic and/or dermatological and/or pharmaceutical composition, comprising cotton honeydew extract, as an active ingredient, within a cosmetically, pharmaceutically or dermatolgically acceptable medium, wherein the extract is dissolved in one or several cosmetically or pharmaceutically acceptable solvents selected from the group consisting of ethanol, propanol, isopropanol, propylene glycol, butylene glycol, dipropylene glycol, ethoxylated diglycols propoxylated diglycols, cyclic polyols, petroleum jelly, vegetable oil, and combinations thereof, and wherein the cotton honeydew extract is present in the composition at a concentration between 0.0001% and 20%, by weight, relative to the total weight of the composition.

10. A cosmetic and/or dermatological and/or pharmaceutical composition comprising a cotton honeydew extract, as an active ingredient, within a cosmetically, pharmaceutically or dermatolgically acceptable medium, wherein the extract is dissolved in a cosmetic or pharmaceutical vector selected from the group consisting of liposomes, adsorbed on powdery organic polymers, mineral supports, talc, and bentonites, and wherein the cotton honeydew extract is present in the composition at a concentration between 0.0001% and 20%, by weight, relative to the total weight of the composition.

11. The composition according to claim 9, wherein the composition is a cosmetic and/or dermatological composition adapted to topical cutaneous application through an acceptable cosmetic or dermatological medium.

12. The composition according to claim 9, wherein the extract is dissolved in a cosmetic or pharmaceutical vector selected from the group consisting of liposomes, adsorbed on powdery organic polymers, mineral supports, talc and bentonites.

13. The composition according to claim 9, wherein the extract is in the form of an oil solution, or the form of an oil-in-water or water-in-oil emulsion or in multiple emulsions.

14. A method for treating keratin substrates consisting of applying to the keratin substrates an effective amount of the composition according to claim 9.

15. A method for treating skin and/or hair against external aggressions consisting of applying to the surface of the skin and/or hair an effective amount of the composition according to claim 9.

16. A method of reinforcing skin protection, increasing keratin synthesis, and/or nourishing keratin substrates, consisting of applying to the skin surface and/or hair an effective amount of the composition according to claim 9.

17. The composition according to claim 10, wherein the composition is a cosmetic and/or dermatological composition adapted to topical cutaneous application through an acceptable cosmetic or dermatological medium.

18. The composition according to claim 9, wherein the extract is in the form of an oil solution, or the form of an oil-in-water or water-in-oil emulsion or in multiple emulsions.

19. A method for treating skin and/or hair against external aggressions consisting of applying to the surface of the skin and/or hair an effective amount of the composition according to claim 10.

20. A method of reinforcing skin protection, increasing keratin synthesis, and/or nourishing keratin substrates, consisting of applying to the skins surface and/or hair an effective amount of the composition according to claim 10.

21. A method for treating keratin substrates consisting of applying to the keratin substrates an effective amount of the composition according to claim 9.

* * * * *